US012590314B2

(12) United States Patent
Merchant et al.

(10) Patent No.: US 12,590,314 B2
(45) Date of Patent: Mar. 31, 2026

(54) EXPRESSING MULTIPLE GENES FROM A SINGLE TRANSCRIPT IN ALGAE AND PLANTS

(71) Applicant: The Regents of the University of California, Oakland, CA (US)

(72) Inventors: Sabeeha S. Merchant, Berkeley, CA (US); Sean David Gallaher, Berkeley, CA (US); Jeffrey L. Moseley, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/065,615

(22) Filed: Dec. 13, 2022

(65) Prior Publication Data
US 2023/0110869 A1 Apr. 13, 2023

Related U.S. Application Data

(63) Continuation of application No. PCT/US2021/043085, filed on Jul. 23, 2021.

(60) Provisional application No. 63/057,877, filed on Jul. 28, 2020.

(51) Int. Cl.
*C12N 15/82* (2006.01)

(52) U.S. Cl.
CPC ..... *C12N 15/8216* (2013.01); *C12N 15/8274* (2013.01)

(58) Field of Classification Search
None
See application file for complete search history.

(56) References Cited

U.S. PATENT DOCUMENTS

| | | | |
|---|---|---|---|
| 9,518,277 B2 * | 12/2016 | Franklin | C12P 7/6463 |
| 9,790,488 B2 * | 10/2017 | Yang | C12N 15/85 |
| 2003/0041353 A1 * | 2/2003 | Daniell | C12N 15/8241 |
| | | | 800/288 |
| 2008/0241916 A1 | 10/2008 | Daniell et al. | |

| | | | |
|---|---|---|---|
| 2016/0244746 A1 | 8/2016 | Yang | |
| 2019/0100780 A1 | 4/2019 | Franklin et al. | |
| 2020/0032302 A1 | 1/2020 | Franklin et al. | |

FOREIGN PATENT DOCUMENTS

| | | | | |
|---|---|---|---|---|
| CN | 108495933 A | * | 9/2018 | ......... C12N 15/8216 |

OTHER PUBLICATIONS

Onishi et al., 2016, Robust transgene expression from bicistronic mRNA in the green alga *Chlamydomonas reinhardtii*. G3 (Bethesda) 6: 4115-4125. (Year: 2016).*

Hernández et al., 2019, Conservation and variability of the AUG initiation codon context in eukaryotes. Trends in biochemical sciences, 44(12), 1009-1021. (Year: 2019).*

Kim, 2017, pHSP70/pRBCS2 combined promoter for C. reinhardtii, Registry of Standard Biological parts, https://parts.igem.org/Part:BBa_K2516001, accessed online Dec. 2, 2024. (Year: 2017).*

Onishi, M., & Pringle, J. R. (2016). Robust transgene expression from bicistronic mRNA in the green alga *Chlamydomonas reinhardtii*. G3: Genes, Genomes, Genetics, 6(12), 4115-4125 (Year: 2016).*

Hernández, G., Osnaya, V. G., & Pérez-Martínez, X. (2019). Conservation and variability of the AUG initiation codon context in eukaryotes. Trends in biochemical sciences, 44(12), 1009-1021 (Year: 2019).*

Deng, Z., Zhang, S., Gu, S., Ni, X., Zeng, W., & Li, X. (2018). Useful bicistronic reporter system for studying poly (A) site-defining cis elements and regulation of alternative polyadenylation. International Journal of Molecular Sciences, 19(1), 279 (Year: 2018).*

Perozeni et al., Turning a green alga red: engineering astaxanthin biosynthesis by intragenic pseudogene revival in Chlamydomonas reinhardtii, 2020, Plant Biotechnology Journal, 18(10), 2053-2067 (Year: 2020).*

International Search Report for priority PCT/US21/43085, 9 pages (Dec. 14, 2021).

Rerozeni et al. "Turning a green alga red: engineering astaxanthin biosynthesis by intragenic pseudogene revival in Chlamydomonas reinhardtii" Plant Biotechnol J, Feb. 25, 2020, vol. 18, No. 10, pp. 2053-2067. Especially, Summary.

* cited by examiner

*Primary Examiner* — Amjad Abraham
*Assistant Examiner* — Jessica Nicole Stockdale
(74) *Attorney, Agent, or Firm* — Richard Aron Osman

(57) ABSTRACT

Multiple exogenous genes are expressed from a single transcript in algae and plants using engineered plant polycistronic loci.

7 Claims, 3 Drawing Sheets pJLM0047    pJLM0048

BKT1_SUC2 reporter    promoter    PGK1 promoter

| Fatty Acid (area %) | HMF | UTEX 250 |
|---|---|---|
| C10:0 | 1.77 | 0.03 |
| C12:0 | 6.13 | 1.14 |
| C14:0 | 6.35 | 0.06 |
| C15:0 | 0.29 | |
| C16:0 | 20.37 | 16.36 |
| C16:1n-9 | 0.36 | |
| C16:1n-7 | 2.85 | 0.74 |
| C17:0 | 0.31 | 0.17 |
| C18:0 | 5.99 | 2.69 |
| C18:1n-9 | 31.13 | 64.76 |
| C18:1n-7 | 2.52 | |
| C18:2n-6 | 12.96 | 11.96 |
| C18:3n-3 | 1.15 | 1.04 |
| C20:0 | 0.19 | 0.30 |
| C20:1n-9 | 0.53 | 0.17 |
| C20:2n-6 | 0.29 | |
| C20:3n-6 | 0.32 | |
| C20:4n-6 | 0.41 | |
| C22:6n-3 | 0.40 | |

Annotations: mid-chain (C10:0–C16:0); palmitic acid (C16:0); palmitoleic acid (C16:1); stearic acid (C18:0); oleic acid (C18:1n-9); vaccenic acid (C18:1n-7); VLC-PUFA (C20:4n-6–C22:6n-3)

sn-1　olein
sn-2　palmitin
sn-3　olein

EXPRESSING MULTIPLE GENES FROM A SINGLE TRANSCRIPT IN ALGAE AND PLANTS

This invention was made with government support under Grant Numbers DE-FC02-02ER63421 and DE-SC0018301 awarded by the U.S. Department of Energy. The government has certain rights in the invention.

INTRODUCTION

"Polycistronic" describes the situation in which two (bi-cistronic/dicistronic), three (tricistronic), or more separate proteins are encoded on a single molecule of mRNA. In prokaryotes, polycistronic expression is the norm. Prokaryotic genes, usually with a shared function or pathway, are clustered into operons that are co-transcribed to generate polycistronic mRNAs. Many viral genomes also employ strategies to encode multiple genes on a common transcript in order to maximize the coding potential of their extremely compact genomes. In contrast, the paradigm of protein expression in eukaryotes has been that genes are expressed monocistronically; that is, each transcript carries a single protein-coding ORF.

Exceptions to the monocistronic expression in eukaryotes paradigm have been identified including the MOCS2 locus in humans and the tomPRO1 locus in tomato. In *Drosophila*, the discovery of a dicistronic heat shock protein locus paved the way for discovery of many more polycistronic loci.

The discovery of polycistronic loci has accelerated with the availability of new methodologies for transcript sequencing and annotation that rely on kbp long reads of whole transcript isomers on the PacBio and Oxford Nanopore platforms (hence Iso-Seq). For instance, transcriptome sequencing in the mushroom-forming fungus, *Plicaturopsis crispa*, revealed 314 loci where two or more annotated genes were co-expressed on polycistronic transcripts. Similarly, a recent study in the cotton plant, *Gossypium arboreum*, used Iso-Seq for structural annotation and found 1115 loci that exhibited evidence of polycistronic expression. In both of these studies, polycistronic expression at these loci was not exclusive; i.e. the genes that were observed on polycistronic transcripts were also identified on monocistronic transcripts. Neither study provided evidence for production of distinct polypeptides from the encoded ORFs.

Green algae have been promoted as vehicles for the production of biofuels, pharmaceuticals, food additives, vaccines, and for toxic substance remediation, and many plants are the focus of efforts to produce drought tolerant, pest resistant, or more nutritious crops. Many of these engineering efforts rely on expression of multiple transgenes (e.g. in a multistep metabolic pathway to avoid accumulation of a toxic intermediate). It can also be useful to produce two or more proteins in a particular stoichiometry, as in a heterodimer that requires equimolar production of two polypeptides. Whether the goal is to express one transgene, or several, most efforts to transform plants and algae require cotransformation of the gene of interest with a selectable marker, such as a gene that confers resistance to a drug or herbicide, or complements an auxotrophy. Unfortunately, commonly used methods for co-transformation of algae and other plants are very inefficient.

Molecular biologists have been interested in expressing multiple proteins from a single mRNA, and prior work describes polycistronic expression in plants using viral elements, mainly IRES and 2A elements:

1) using a viral 2A element in rice: e.g. Sun-Hwa Ha, et al. *Stepwise Pathway Engineering to the Biosynthesis of Zeaxanthin, Astaxanthin and Capsanthin in Rice Endosperm*. Metab Eng. 2019 March; 52:178-189;

2) comparing expression vectors that use an IRES versus a 2A element in rice: e.g. Sun-Hwa Ha, et al. Application of two bicistronic systems involving 2A and IRES sequences to the biosynthesis of carotenoids in rice endosperm. Plant Biotechnology Journal. Vol. 8, Issue 8, October 2010. Pages 928-938;

3) using a linker sequence to confer polycistronic expression in tobacco: e.g. Tony Lougha, et al. *Expression of genes in transgenic plants from bicistronic transcriptional units*. Plant Science Volume 129, Issue 1, 28 Oct. 1997, Pages 91-99;

4) producing a polycistronic expression vector for use in algae (*Chlamydomonas reinhardtii*), demonstrating expression of two proteins (CrVenus-3FLAG and APHVIII) in vivo in the alga—the report does not quantify the proteins that are produced from this construct, nor suggest or propose any method for altering the ratio of the two proteins; e.g. Masayuki Onishi et al. *Robust Transgene Expression from Bicistronic mRNA in the Green Alga Chlamydomonas reinhardtii*. G3: GENES, GENOMES, GENETICS. Dec. 1, 2016 vol. 6 no. 12 4115-4125;

5) using polycistronic expression vectors in algae that are based on a viral (foot-and-mouth-disease-virus) 2A element; e.g. Beth A. Rasala, et a., *Enhanced Genetic Tools for Engineering Multigene Traits into Green Algae*. PLOS One. Apr. 7, 2014.

SUMMARY OF THE INVENTION

We disclose that polycistronic gene expression provides a valuable tool to help achieve many of these objectives for transgene expression including multiple practical applications:

1) Increasing the number of transformants that express the gene of interest. By placing a selectable marker gene (e.g. drug resistance, herbicide resistance, etc.) in the downstream spot, and a gene of interest in the upstream spot in a polycistronic expression vector, the majority of drug or herbicide resistant colonies or seeds will also express the gene of interest. This reduces the number of clones or plants that must be screened to find one that expresses the gene of interest.

2) Maintaining expression of the gene of interest. Many algae, such as *C. reinhardtii*, have mechanisms for silencing transgene expression. Constructs such as the one described above (gene of interest upstream, selectable marker gene downstream) help mitigate this because any effort to silence transcription or degrade the mRNA will cause the transformant to be lost under drug selection. Thus, maintaining positive transformants in the presence of the drug impedes efforts by the cell to silence the transgene, i.e. some mechanisms work by degrading the mRNA, so positioning the selectable marker and protein of interest on the same transcript can impede silencing.

3) Increasing expression of the gene of interest. Some drug selectable markers, such as the cry1-1 allele which encodes an emetine-resistant form of RPS14, confer resistance to the drug in proportion to their level of expression. This means that ramping up the concentration of the drug will select for ever increasing expression of the drug-resistance gene. Placing the cry1-1 allele downstream of a gene of interest in a polycistronic vector means that increasing concentrations of emetine will select for increasing expression of the gene of interest. Hence we documented two proteins of the correct size in vitro when we replaced the downstream ORF of a polycistronic construct with the cry1-1 allele.

4) Expression of a multimer, such as heterotrimer or heterodimer, particularly wherein the subunits are advantageously expressed in predetermined stoichiometry, such as 2:1 or 1:1 or 1:1:2, etc.

5) Expression of two or more proteins that catalyze different steps in a metabolic pathway. In efforts to introduce new metabolic functions to a bioengineered organism, it is often ideal to have simultaneous expression of all the components of that biosynthetic pathway. This allows for tunable and/or inducible expression of that pathway, and can help avoid the accumulation of toxic intermediates. Expressing the necessary genes on a polycistronic expression vector is an effective way to achieve coordinated expression.

Producing multiple proteins from a single mRNA has been a long-standing objective; we show how to achieve this using the organism's own sequences, without recourse to viral elements or other foreign elements, which is important for any technology where bioproducts are generated, since these may be used on humans (cosmetics) or in humans (food additives), especially crop technology.

Accordingly, the invention provides plants and methods for expressing multiple exogenous genes from a single transcript in algae and plants using engineered plant polycistronic loci.

The invention is particularly applicable to bioengineering efforts that rely on expression of multiple transgenes (e.g. in a multi-step metabolic pathway to avoid accumulation of a toxic intermediate), such as the production of biofuels, pharmaceuticals, vaccines, and for toxic substance remediation.

The invention is also useful to produce two or more proteins in a particular stoichiometry, as in a heterodimer that requires equimolar production of two polypeptides. Polycistronic expression vectors that incorporate 2A elements necessarily produce nearly equimolar amounts of each protein, but this can be undesirable in some circumstances (e.g. where one of the proteins becomes toxic at the high levels). We have shown, and the invention provides fine-tuning of the ratio of the different proteins that are expressed by our method (e.g. 1:1, 1:3, etc), which facilitates a wider range of experimental and engineering designs.

In an aspect, the invention is a plant transformed with a polycistronic plant locus encoding polycistronically-expressed exogenous proteins.

In embodiments:

the polycistronically-expressed exogenous proteins;

expression of the proteins is regulated by a polycistronic gene expression regulatory element native to the plant;

expression of the proteins is regulated by a polycistronic gene expression regulatory element native to a different plant species;

expression or translation of the proteins is regulated by a plant polycistronic gene expression regulatory element, exclusive of any viral, foreign or other non-plant elements;

one of the proteins is a selectable marker, such as a protein that confers resistance to a drug or herbicide, or complements auxotrophy;

the plant is selected from crop species, selected from cereal crops, starchy root and tuber crops, legume crops and plant oil crops;

the plant is selected from wheat, corn, rice, sorghum, potato, cassava, soybeans, peas, rapeseed, palm, peanut;

the plant is selected from an alga, such as *Chlorella, Nannocholoropsis, Botryococcus*, and *Dunaliella;* the plant comprises a corresponding polycistronic mRNA transcribed from the locus and comprising open reading frames (ORFs) for each of the exogenous proteins, wherein translation of each of the ORFs is regulated by corresponding translation initiation sites tuned to effect a predetermined ratio of the proteins;

the plant comprises a corresponding polycistronic mRNA transcribed from the locus and comprising open reading frames (ORFs) for each of the exogenous proteins, wherein translation of each of the ORFs is regulated by corresponding translation initiation sites tuned to effect a predetermined ratio, that is non 1:1, of the proteins;

the plant is *Auxenochlorella prototothecoides*, wherein the locus expresses a polycistronic transcript encoding heterologous proteins;

the plant is *Auxenochlorella prototothecoides*, wherein the locus expresses a polycistronic transcript encoding heterologous proteins, the transcript comprising SUC2, encoding sucrose invertase from *Saccharomyces cerevisiae* used as a selectable transformation marker, wherein SUC2 catalyzes the hydrolysis of sucrose in the growth medium into glucose and fructose, which can be assimilated to support heterotrophic growth, and BKT1, encoding a beta-carotene ketolase (BKT1) from *Chlamydomonas*, wherein the BKT1 is targeted to the plastid, where it converts lutein and zeaxanthin into the red keto-carotenoids 4-keto lutein and astaxanthin for visual detection, wherein the SUC2 and BKT1 are operatively expressed by a promoter selected from Auxenochlorella HUP1 hexose transporter gene and PGI1 phosphoglycerate isomerase 1 gene, or an inducible promoter selected from 1) an ammonium transporter promoter (AMT1), which is activated under nitrogen deficiency, and 2) a vitamin B12-independent methionine synthase promoter (METE), which is repressed in the presence of vitamin B12; and/or the plant is *Auxenochlorella prototothecoides*, wherein the locus expresses a polycistronic transcript encoding heterologous proteins, the transcript encoding (a) a FATB2 thioesterase from *Cuphea wrightii*, which has peak specificity for cleavage of lauryl-ACP, and shoulders of activity against caproyl-ACP and myristoyl-ACP, provides the mid-chain fatty acids; and (b) a *Chlamydomonas* lysophosphatidic acid acyltransferase 2 (LPAAT2), which specifically incorporates C16 fatty acids at the sn-2 position in TAG, and alters the native Auxenochlorella TAG structure, which favors mono- and polyunsaturated C18 fatty acids at sn-2, wherein knock-in of the locus at an allele of the Auxenochlorella stearoyl-ACP desaturase 2 gene (SAD2) simultaneously increases accumulation of mid-chain and stearic fatty acids, along with C16:0 incorporation at sn-2, producing TAGs which partially mimic human milk fat (HMF).

In an aspect the invention provides a method of recombinant protein production, comprising growing a plant herein, under conditions wherein the plant expresses the proteins.

The invention encompasses all combinations of the particular embodiments recited herein, as if each combination had been laboriously recited.

DESCRIPTION OF PARTICULAR EMBODIMENTS OF THE INVENTION

Figures 1, 2:
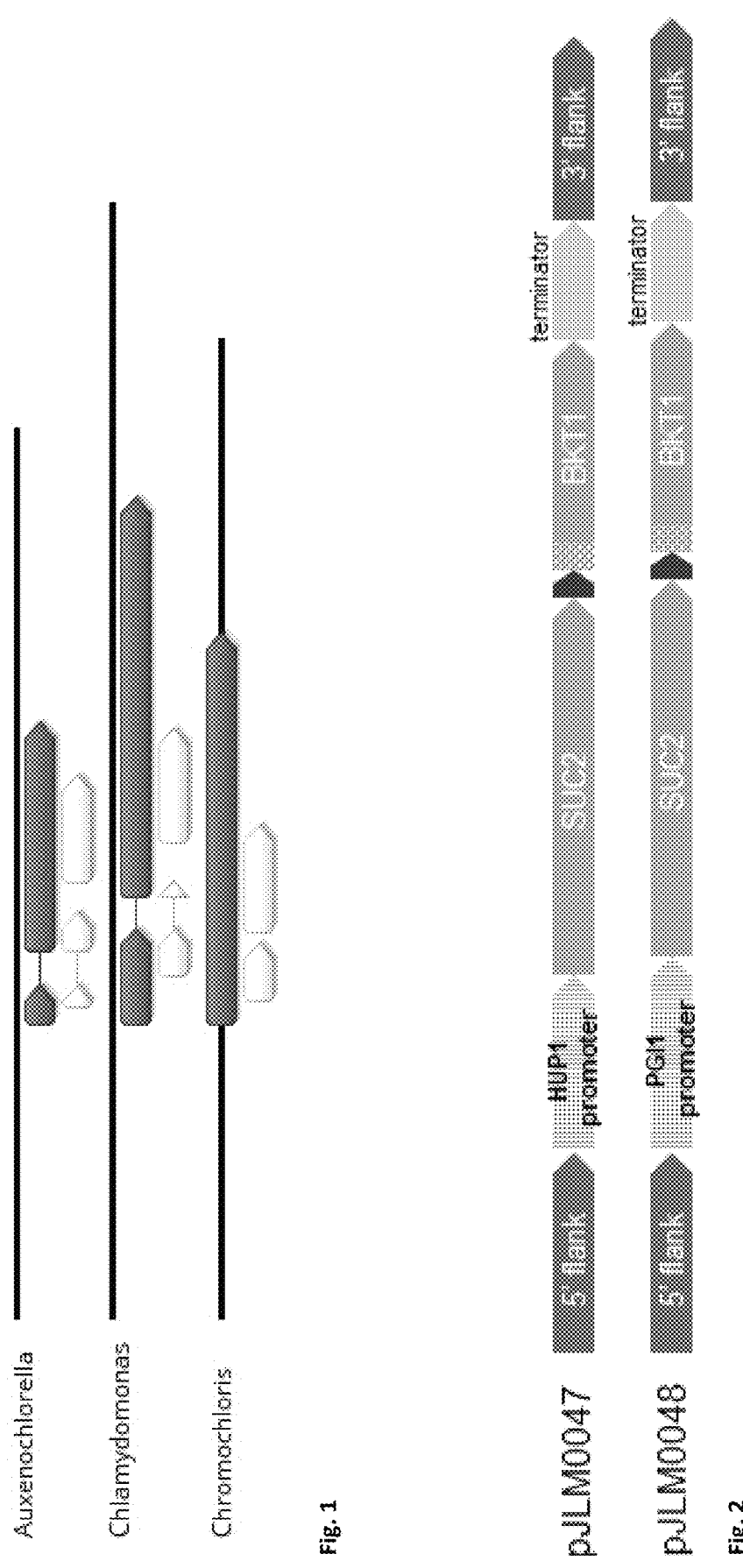
FIG. 1. Schematic comparing the TOM22-SDHAF3 polycistronic loci in *A. protothecoides, C. reinhardtii* and *C. zofingiensis*. Thick black lines denote the genomic sequence. Transcripts are presented in dark grey. Thin black lines represent introns, and coding sequences are white.
FIG. 2. DNA constructs to disrupt allele 2 of the endogenous Auxenochlorella lycopene cyclase epsilon gene (LCYE-2), and express SUC2 and BKT1. LCYE-2 5' and 3' flanks targeting homologous recombination at LCYE-2 are shaded dark grey. The promoter in pJLM0047 is from the Auxenochlorella HUP1 hexose transporter gene; in pJLM0048 promoter is from the PGI1 phosphoglycerate isomerase 1 gene. Promoter regions are indicated with vertical stripes; the SUC2 and BKT1 CDS are shaded medium grey; the interORF sequence from Auxenochlorella TOM22-SDHAF3 is shaded black; and a sequence encoding the SAD2 transit peptide is shaded with a trellis pattern. The SAD2 terminator region, containing the 3' UTR, is shaded light grey.

Unless contraindicated or noted otherwise, in these descriptions and throughout this specification, the terms "a" and "an" mean one or more, the term "or" means and/or. The examples and embodiments described herein are for illustrative purposes only and various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Examples: Applications of Polycistronic Expression

We have developed *Chromochloris zofingiensis* as another reference organism for dissecting central carbon metabolism, nutrient physiology and signaling. *C. zofingiensis* is likely separated from *C. reinhardtii* by over 541 million years of evolution, but both species share a number of characteristics that make them invaluable for research. While both species have high quality, chromosome-scale genome assemblies, functional and systems biology studies are hindered by misannotations in their structural gene annotations. In an effort to improve these, we sought to describe the transcriptome with Iso-Seq on the PacBio platform. The analysis revealed pervasive polycistronic transcripts in both species. We observed 173 exclusively polycistronic loci in *C. zofingiensis*, and 87 in *C. reinhardtii*. Many more loci were incompletely polycistronic (i.e. both monocistronic and polycistronic transcripts were evident). Many of the polycistronic loci are evolutionarily conserved between *C. reinhardtii* and *C. zofingiensis*, and in other chlorophytes. In this work, we employ a variety of complementary in vivo and in vitro approaches to validate that hundreds of genes in these two chlorophyte species are expressed on polycistronic transcripts.

Identification of polycistronic expression in two divergent algal species.

In an effort to improve the structural gene annotations of two reference chlorophyte organisms, *C. reinhardtii* and *C. zofingiensis*, we used long read, single molecule sequencing of cDNAs on the PacBio Sequel platform (Iso-Seq). Data analysis for both organisms revealed hundreds of loci in which Iso-Seq reads overlapped with two or more ORFs. After extensive manual curation, the list was pared to 87 loci in *C. reinhardtii* and 173 loci in *C. zofingiensis* in which two or more genes were consistently found to be associated with a single transcript. Browser views of example bicistronic gene pairs in *C. reinhardtii* and *C. zofingiensis* were generated. In addition to the ORFs that were exclusively expressed as polycistronic transcripts, we noted many other loci in which either the upstream ORF, the downstream ORF or both could be found on both monocistronic and polycistronic transcripts. For *C. reinhardtii*, we identified as many fully polycistronic loci as partially polycistronic loci. For this study, we focused on the 87 loci in *C. reinhardtii* and the 173 loci in *C. zofingiensis* that were transcribed exclusively on polycistronic transcripts to assess whether they represent genuine polycistronic genes, as opposed to artifacts of the Iso-Seq methodology. Several criteria, as described below, were used to establish the authenticity of the polycistronic mRNAs.

Polycistronic genes are smaller and more closely spaced than monocistronic genes.

First, we compared the properties of the candidate polycistronic loci relative to monocistronic ones. Both the upstream and downstream ORFs are significantly smaller than the ORFs of the monocistronic genes. This was especially pronounced for the upstream polycistronic genes of *C. zofingiensis*. We quantified the inter-ORF distance for colinear genes (defined here as genes on the same strand of the same chromosome with ≤20 kbp separation between ORFs), and plotted the distribution of these for monocistronic and polycistronic gene pairs. Polycistronic gene pairs were dramatically closer to each other as compared to other colinear gene pairs.

Stop codon usage and reading frame are consistent with separate ORFs.

ORFs are delineated by start and stop codons. We considered the possibility that the putative multiple ORFs within a transcript could encode a single protein by means of stop codon readthrough. The stop codon of the upstream gene is one factor (the other is a shared reading frame) that separates the upstream ORF from the downstream one. Therefore, we examined the proportion of ochre, amber, and opal stop codons for polycistronic upstream and downstream genes, and compared these with the proportions for monocistronic genes. Opal stop codons were employed in the plurality of genes, with only minor differences between the polycistronic and monocistronic genes. Stop codon usage for upstream polycistronic genes was not significantly different from that of other genes.

Next, we assessed the relative reading frames of the upstream ORF versus the downstream one. Two ORFs were considered to be in-frame if the inter-ORF sequence was perfectly divisible by 3. In both algae, we found that about ⅓ of the time the ORFs were in-frame, which would be expected by chance. Taken together, these patterns argue against the read-through hypothesis.

Genes in polycistronic loci are highly coexpressed, with a shared promoter and poly(A) tail.

Genuinely polycistronic mRNAs should result from a single promoter upstream of the most 5' located ORF whereas artefactual polycistronic transcripts (resulting from errors in reverse transcription and library preparation) would result from multiple independent promoters for each gene. We used three criteria to support the former model.

First, we sought to map promoter regions of candidate polycistronic transcripts using Chromatin Immunoprecipitation and Sequencing (ChIP-Seq) with an anti-H3K4me3 Ab, because tri-methylation of lysine 4 on histone 3 (H3K4me3) has been shown to be a highly stable epigenetic marker for transcription start sites in *C. reinhardtii*. The coverage of immunoprecipitated sequencing reads was compared with the coverage of input sequencing reads and used to calculate a per-base score of H3K4me3 enrichment for the entire genome. This was plotted as "H3K4me3" track. The mean H3K4me3 enrichment score was calculated for the first 500 bp of each gene, and the distribution of these scores was plotted as a box plot for monocistronic, polycistronic upstream, and polycistronic downstream genes. The mean score for polycistronic upstream genes (47.7) was not significantly different to that for monocistronic genes (40.1). In contrast, polycistronic downstream genes had a dramatically lower mean score of 1.0. This confirmed that for these 87 loci, transcription initiation was occurring exclusively at the start of the upstream gene.

Second, we surveyed the occurrence of poly(A) tails and the polyadenylation signal associated with the transcript. If a pair of colinear genes is exclusively expressed as a polycistronic transcript, it would be expected that the downstream, but not the upstream gene would have a poly(A) tail. By this logic, upstream genes in polycistronic gene pairs would be expected to have fewer polyadenylation signal sequences than the corresponding downstream genes. The most frequently used signal for *C. reinhardtii* is "UGUAA" (Shen et al., 2008, *Unique features of nuclear mRNA poly (A) signals and alternative polyadenylation in Chlamydomonas reinhardtii. Genetics* 179, 167-176). To determine if the same PAS was used by *C. zofingiensis*, we quantified all 5-mers within the 3' termini of *C. zofingiensis* transcripts. The same sequence, "UGUAA", was observed at more than double the frequency of any other 5-mer. All genes were scored for the presence of "UGUAA" within the final 100 bps of the transcript sequence. This generous range was used because we had evidence of widespread alternative poly(A) tailing of transcripts from the Iso-Seq data, and we wanted to capture putative polyadenylation signal sequences from loci upstream of the annotated 3' ends of the transcripts. The fraction of genes with a polyadenylation signal were sorted into polycistronic upstream, polycistronic downstream, and monocistronic (i.e. the remaining) genes. Given the relative GC-content of the two species, we calculated the expected frequency of a "UGUAA" 5-mer to occur by chance in a sequence of 100 bps. The actual frequency of polyadenylation signals in polycistronic genes is nearly identical to the frequency in monocistronic genes. In contrast, the frequency in polycistronic upstream genes was dramatically lower, and much lower than would be expected by random chance.

We used Iso-Seq data to assess transcript polyadenylation. The 100 nucleotides immediately upstream of a stretch of 8 or more As was computationally isolated from the untrimmed Iso-Seq reads, mapped to the genome, and quantified relative to the total number of Iso-Seq reads that mapped to the same loci.

Consistent with the idea that the 87 loci in *C. reinhardtii* and the 173 loci in *C. zofingiensis* are expressed as polycistronic transcripts with a single 3' poly(A) tail, we observed almost no poly(A)-adjacent reads mapping to the 3' ends of the upstream genes (0.1%). In contrast, we observed comparable numbers of poly(A)-adjacent reads in polycistronic downstream genes (85.6%) as was observed for monocistronic genes (86.8%).

Third, we estimated the abundance of transcripts for each gene individually, i.e. regardless of polycistronic or monocistronic expression, from RNA-Seq datasets. For a true polycistronic mRNA, we expect nearly identical abundance estimates for upstream and downstream genes. To test this, we calculated Pearson Correlation Coefficient (PCC) values to compare the similarity in transcript abundance estimates for polycistronic gene pairs across a wide range of conditions. For comparison, we also calculated PCC values for all colinear gene pairs. The median PCC value for the polycistronic gene pairs 0.97 (i.e. nearly perfect correlation). PCC values for the other colinear gene pairs were widely distributed between +1 and −1, with a median value of 0.02.

From these results taken together (a single promoter, a single poly(A) tail, and equal abundance of transcripts for each ORF), we conclude that the 87 and 173 transcripts in *C. reinhardtii* and *C. zofingiensis* are authentic and exclusively polycistronic.

The polycistronic loci are unlikely to be misidentified selenoproteins.

In genes that encode selenoproteins, the UGA stop codon is repurposed to code for a selenocysteine. As such, the Sec codon is typically mis-identified as a stop codon by commonly used gene prediction tools. This raised the possibility that some or all of the polycistronic transcripts identified in this work were in fact selenoproteins. For polycistronic loci to be mischaracterized selenoproteins genes, (1) the upstream and downstream ORFs would have to be in the same reading frame, and (2) the two ORFs would have exclusively UGA stop codons between them. Only 11 out of 87 polycistronic loci in *C. reinhardtii*, and 15 out of 173 polycistronic loci in *C. zofingiensis* met both criteria. However, SECISearch3 (Mariotti et al., Nucleic Acids Research, 2013), which identifies a distinctive stem loop structure in selenoproteins transcripts called the SECIS element, failed to identify such an element in any of these 26 loci. Furthermore, none of the ORFs in the 26 loci showed significant sequence similarity to any known selenoproteins when evaluated by Seblastian. On the other hand, seven monocistronic *C. zofingiensis* genes were identified with SECIS elements and homology to known proteins. We conclude that none of the UGA-containing polycistronic loci corresponds to a selenoprotein.

Identification of peptides from upstream and downstream genes validates that both ORFs are translated.

Having demonstrated that the upstream and downstream polycistronic genes are co-transcribed onto a common mRNA, we questioned whether both ORFs are translated. We queried pools of proteomics data for both *C. reinhardtii* and *C. zofingiensis* to identify peptides corresponding to proteins derived from any of the ORFs within candidate polycistronic mRNAs. The proteomic libraries used for this study were prepared from trypsin-digested total protein extracts. Besides identifying internal peptides, we could also identify N-terminal peptides (those with an N-terminal Met that is not immediately downstream of a Lys or Arg codon in the predicted ORF) or C-terminal peptides (those with a C-terminal residue that is adjacent to a stop codon in the predicted ORF). An example of a polycistronic locus from *C. zofingiensis* in which multiple distinct peptides were found from both the upstream and downstream ORF was generated. Not only do the peptides validate that both ORFs are translated, we observed a C-terminal peptide for the upstream ORF, and an N-terminal peptide for the downstream ORF, confirming separate synthesis/translation of each protein.

Considering all polycistronic loci, we detected at least one unambiguously assigned peptide from 56% of the upstream ORFs and 56% of the downstream ORFs for *C. reinhardtii*. For *C. zofingiensis*, we detected peptides from 42% of the upstream ORFs and 52% of the downstream ORFs. This is less than the percentage of monocistronic genes that were detected: 72% and 82% for *C. reinhardtii* and *C. zofingiensis*, respectively. However, the polycistronically-expressed proteins are significantly smaller than monocistronic proteins and smaller proteins are detected at a lower frequency than larger proteins.

The percentage of polycistronic proteins that could be identified by an N-terminal or C-terminal peptide was also examined. In *C. reinhardtii*, an N-terminal peptide was detected for 8% of the polycistronic downstream ORFs (compared to 4% of monocistronic ORFs) and a C-terminal peptide was detected for 7% of the polycistronic upstream ORFs (compared to 7% for monocistronic ORFs). In *C. zofingiensis*, 5% of polycistronic downstream ORFs were identified by an N-terminal peptide and 4% of polycistronic upstream ORFs were identified by a C-terminal peptide. These results are consistent with independent translation of two separate ORFs, as opposed to post-translational splicing of a single polypeptide.

In vitro transcription and translation recapitulate polycistronic expression and demonstrates expression of reporter and drug-selectable genes.

The proteomic data above validate the polycistronic functionality of the mRNAs in vivo in algal systems. To assess whether polycistronic mRNAs can be translated in classic in vitro systems, we generated constructs for several polycistronic gene pairs, and subjected them to coupled in vitro transcription and translation in wheat germ extract. The radiolabeled translation products, separated by SDS-PAGE, were visualized by fluorography. We identified pairs of translation products at or near the predicted sizes corresponding to the ORFs for six constructs: three from *C. reinhardtii* and three from *C. zofingiensis* (Table A).

To distinguish whether foreign sequences could be translated from these mRNAs, we replaced the upstream or downstream ORFs or both with a gene encoding a reporter protein (m Venus, derived from YFP) or a drug-selectable protein (ribosomal protein RPS14-Em$^R$, which confers resistance to the drug emetine, Nelson, et al., 1994, *The CRY1*

*gene in Chlamydomonas reinhardtii: structure and use as a dominant selectable marker for nuclear transformation. Mol. Cell. Biol.* 14, 4011-4019). Again, we noted correct synthesis of m Venus from either the upstream or downstream position in the polycistronic mRNA from *C. zofingiensis* Cz02g12225/Cz02g12220 (Table B). Similarly, the intergenic region from a bicistronic gene pair in *C. reinhardtii* (Cre10.g466000/Cre10.g465950) was sufficient to co-express both m Venus and RPS14-Em$^R$.

Role of Kozak-like sequence.

We used the in vitro translation system to test whether the synthesis of the downstream ORF depends on the synthesis of the upstream one. One mechanism for assessing this is to modify the Kozak-like sequence of the upstream ORF. We modified the endogenous sequence associated with ORF Cz02g35025 to be stronger or weaker Kozak-like sequences (based on computational analysis of all Kozak-like sequences in *C. zofingiensis*). The endogenous sequence produced a 1:1 ratio of upstream and downstream products. Strengthening the Kozak sequence changed the ratio to 3:1 and weakening it changed to 0.5:1.

Polycistronic loci are conserved in the green algal lineage.

When genetic features are conserved between species that diverged hundreds of millions of years ago, those features are likely to play an important role in the physiology of those species. Given that we had observed pervasive polycistronic expression in two Chlorophytes, we wished to determine if the phenomenon extends beyond those species. The protein sequences encoded by polycistronic loci in *C. reinhardtii* and *C. zofingiensis* were used as queries in a search for candidate polycistronic loci in five other Chlorophyte species: *Coccomyxa subellipsooidea, Dunaliella salina, Ostreococcus lucimarinus, Micromonas pusilla*, and Volvox, carteri. A phylogenetic tree demonstrates the evolutionary distance between these species. For *C. reinhardtii*, we identified candidate polycistronic loci (two or more adjacent ORFs in at least one other species with significant sequence similarity to a pair of polycistronic ORFs in *C. reinhardtii*) for 21 out of 87 polycistronic loci. The most candidate polycistronic loci, 12, were found in the most closely related species, *V. carteri*. Five polycistronic loci from *C. reinhardtii* had matches in three or more species. When sequences from *C. zofingiensis* were used as the query, 49 out of 173 polycistronic loci had pairs of colinear hits in the other species. The most hits, 27, were found in *D. salina*. 11 polycistronic loci were identified as reciprocal hits between *C. reinhardtii* and *C. zofingiensis*.

The observation of colinear orthologs of polycistronic genes in the other Chlorophyte species is suggestive, but not dispositive that these genes are expressed on polycistronic transcripts in the other species. However, Iso-Seq data from one of the other chlorophyte species, *D. salina*, validated that conserved, colinear ORFs were expressed on polycistronic transcripts for five loci. In the absence of Iso-Seq data, expressed sequence tag (EST) data in *V. carteri, D. salina, C. subellipsoidea* provided additional evidence that colinear orthologs are at least partially expressed on polycistronic transcripts for 15 unique, conserved loci.

Functional significance of polycistronic expression.

Given that polycistronic expression is conserved, what could be the functional significance of expressing two or more ORFs from a single transcript? One locus in *C. reinhardtii* (Cre16.g683483/Cre16.g6834950) called REX1, was first described in 2003. At this locus, a single transcript encodes two proteins, REX1-S and REX1-B, both of which are involved in DNA repair. The smaller of the two ORFs (Cre16.g683483), which encodes REX1-S, is not annotated in the current *C. reinhardtii* gene annotations. The REX1 bicistronic locus from *C. reinhardtii* is conserved in *C. zofingiensis*.

In an effort to assign a function to the remaining polycistronic loci, their protein sequences were searched for conserved domains. No conserved domain could be identified for the majority of polycistronically-expressed gene products for *C. reinhardtii* (56%) or *C. zofingiensis* (57%). As a result, only 17% of *C. reinhardtii* polycistronic transcripts and 22% of *C. zofingiensis* polycistronic transcripts had identifiable domains in all ORFs.

While the functional significance of most polycistronic loci remains unclear, some loci were found to contain functional domains that suggested a possible shared or complementary function. A bicistronic locus from *C. reinhardtii* (Cre12.g513254/Cre12.g513245) expresses two proteins that may be involved in the related functions of DNA repair (a DNA cross-link repair 1A protein) and mitosis (an anaphase-promoting complex subunit 15 protein). Another bicistronic locus was found to be conserved in *C. reinhardtii* (Cre06.g278242/Cre06.g278345), *C. zofingiensis* (Cz13g11085/Cz13g11090) and in 4 other Chlorophyte species. This locus appears to encode two proteins important in the mitochondrion: one that assists in TOM complex assembly and another that facilitates the assembly of succinate dehydrogenase.

We tested the efficacy of artificial polycistronic transcripts in vivo using a heterologous alga, *Auxenochlorella protothecoides* UTEX 250. First, we identified polycistronic loci that were conserved between *Chlamydomonas* and *Chromochloris* and *Auxenochlorella* (diverged by ~650 million years from *Chlamydomonas*/Chromochloris). The genes encoding TOM22 and SDHAF3 are illustrated in FIG. 1. At each locus the TOM22 ORF is upstream and the SDHAF3 ORF is downstream, but there is no sequence conservation in the interORF regions between species.

Next, we designed constructs to express polycistronic transcripts encoding heterologous proteins in *Auxenochlorella*; SUC2, encoding sucrose invertase from *Saccharomyces cerevisiae* can be used as a selectable transformation marker in *Auxenochlorella*, which is unable utilize sucrose or any other disaccharide with the exception of trehalose as a carbon source. A secreted protein, SUC2 catalyzes the hydrolysis of sucrose in the growth medium into glucose and fructose, which can be assimilated to support heterotrophic growth. The synthetic SUC2 coding sequence (U.S. Pat. No. 8,633,012[1]), was codon-optimized for expression in *Prototheca moriformis* UTEX 1435, which is closely related to *A. protothecoides*. Similarly, a sequence encoding a truncated version beta-carotene ketolase (BKT1) from *Chlamydomonas* with improved activity, described by Perozeni et al (2020)[2], was optimized using the *P. moriformis* codon bias. BKT1 is targeted to the plastid, where it converts lutein and zeaxanthin into the red keto-carotenoids 4-keto lutein and astaxanthin for easy visual detection. Constructs for co-expression of SUC2 and BKT1 on polycistronic transcripts are illustrated in FIG. 2.

Figures 3, 4:
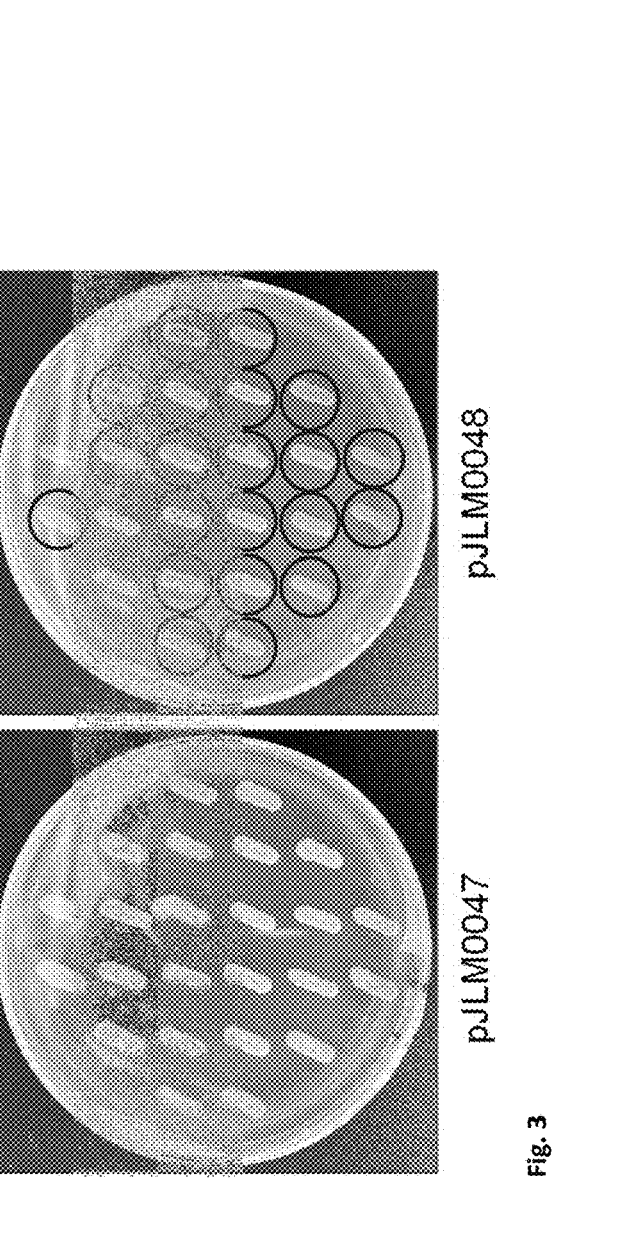
FIG. 3. Transformants grown heterotrophically on media with 2% sucrose as the sole carbon source. Black circles indicate colonies with orange/pink coloration resulting from accumulation of red keto-carotenoids.
FIG. 4. DNA constructs to target SUC2 and BKT1 reporters to the Auxenochlorella LCYE-2 locus. LCYE-2 5' and 3' flanks enabling homologous recombination at LCYE-2 are shaded dark grey. The inducible AMT1 and METE promoters, indicated with vertical stripes, control expression of polycistronic mRNA with the BKT1 CDS in the upstream position and SUC2 in the downstream position. The SUC2 and BKT1 CDS are shaded medium grey: the interORF sequence from Auxenochlorella TOM22-SDHAF3 is shaded black; and a sequence encoding the SAD2 transit peptide is shaded with a trellis pattern. The terminator for the polycistronic gene is from the enolase (PGH) locus (shaded light grey). A cassette for selection of transformants using a neomycin resistance gene (neoR) regulated by the Auxenochlorella phosphoglycerate kinase 1 (PGK1) promoter and terminator, confers resistance to G418 antibiotic.

Constructs pJLM0047 and pJLM0048 were transformed into *A. protothecoides* UTEX 250 and selected for heterotrophic growth (in the dark) on medium containing sucrose as the sole carbon source. Colonies were visible for the transformation with pJLM0047 within 7 days and were large enough to transfer to fresh plates by 12 days, indicating that the HUP1 promoter was effective at driving SUC2 expression. Heterotrophic pJLM0047 colonies were yellow, suggesting that there was limited translation of the downstream BKT1 ORF. Conversely, pJLM0048 transformants took more than 4 weeks to form colonies large enough to transfer to fresh plates, and the majority of those colonies were orange/pink in color, indicating that a significant proportion of yellow lutein & zeaxanthin were converted into red keto-carotenoids by active BKT1. These observations demonstrate the effects of manipulating Kozak sequences on in vitro translation of polycistronic transcripts presented in FIG. 3, insofar as there is a negative correlation between the activity of the gene products from the upstream and downstream ORFs in vivo.

In additional experiments we demonstrate regulated expression of polycistronic BKT1 and SUC2 using inducible promoters. Neomycin resistance provides the selection for transformation so that colony formation is not dependent on SUC2 activity. The constructs illustrated in FIG. 4 drive expression of the polycistronic transcript with 1) an ammonium transporter promoter (AMT1), which is activated under nitrogen deficiency, and 2) a vitamin B12-independent methionine synthase promoter (METE), which is repressed in the presence of vitamin B12. These constructs demonstrate the in vivo effects of manipulating the Kozak sequences of the upstream and downstream ORFs. In this case BKT1 is encoded by the upstream ORF, providing an inverse correlation between the accumulation of red keto-carotenoids and SUC2 activity.

Figure 5:
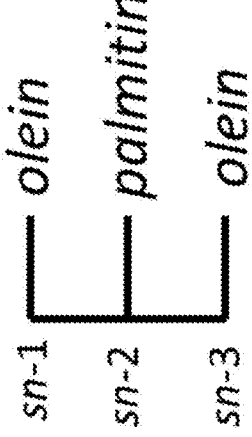
FIG. 5. Average fatty acid composition of HMF compared to average of three lots of *A. protothecoides* UTEX 250 refined, bleached and deodorized oil. Fatty acids percentages that differ significantly between HMF and Auxenochlorella are in bold text and shaded grey. The schematic shows the structure of 1,3-olein-2-palmitin.

We also demonstrate a practical application of polycistronic gene expression in *Auxenochlorella* by engineering strains to mimic human milk fat (HMF). FIG. 5 shows an average fatty acid composition of HMF triacylglycerides (TAGs), compiled from Yuhas et al, 2006[3], compared to an average of three lots of *Auxenochlorella* oil (GRAS No. 384). HMF is enriched in mid-chain fatty acids, palmitic and stearic acid and very-long-chain polyunsaturated fatty acids, compared to the algae-derived oil. A key feature of HMF composition is that 70% of the palmitic acid is in the sn-2 position, which is important for infant digestion[4]. We use polycistronic genes to co-express two activities: 1) the FATB2 thioesterase from *Cuphea wrightii*, which has peak specificity for cleavage of lauryl-ACP, and shoulders of activity against caproyl-ACP and myristoyl-ACP[5,6], provides the mid-chain fatty acids; and 2) the *Chlamydomonas* lysophosphatidic acid acyltransferase 2 (LPAAT2), which specifically incorporates C16 fatty acids at the sn-2 position in TAG, and alters the native *Auxenochlorella* TAG structure, which favors mono- and polyunsaturated C18 fatty acids at sn-2[7]. Our knock-in of polycistronic expression constructs encoding these two activities at one or the other allele of the *Auxenochlorella* stearoyl-ACP desaturase 2 gene (SAD2) can simultaneously increase accumulation of mid-chain and stearic fatty acids, along with C16:0 incorporation at sn-2, producing TAGs which partially mimic HMF.

Comparison with Polycistronic Expression in Other Species

Polycistronic expression in trypanosomes and nematodes requires the transplicing of a spliced leader sequence upstream of each ORF. We observed no evidence of transplicing in the Iso-Seq data for either *C. reinhardtii* or *C. zofingiensis*. The Iso-Seq protocol was performed using poly(A) selected mRNA; thus, it represents a snapshot of all mature, polyadenylated mRNA that was present in the cell when the RNA was collected. Transplicing, if it had been present, should have been readily observable as soft-clipped bases in alignments of the Iso-Seq data to the genome assembly. Thus, the phenomenon described in this work appears to be wholly different than the polycistronic expression described in nematodes and trypanosomes.

Recently, polycistronic expression was observed in mushroom forming fungi and in cotton. In both studies, polycistronic expression was "incomplete"; specifically, polycistronic loci were also expressed monocistronically. For the purpose of this work, we chose to focus on the 87 loci in *C. reinhardtii* and the 173 loci in *C. zofingiensis* for which the observed expression was exclusively polycistronic. However, it is worth noting that we identified at least 87 additional loci in *C. reinhardtii* in which both monocistronic and polycistronic expression was observable. At these loci, some fraction of the Iso-Seq reads included two or more ORFs, but some additional fraction of Iso-Seq reads were smaller and included only the upstream or downstream ORF. The presence of both partially and completely polycistronic loci in the two chlorophyte species distinguishes this work from the prior studies in cotton and fungi.

1. Franklin, S. et al. Tailored oils produced from recombinant oleaginous microorganisms. (2014).
2. Perozeni, F. et al. Turning a green alga red: engineering astaxanthin biosynthesis by intragenic pseudogene revival in *Chlamydomonas reinhardtii*. Plant Biotechnol. J. 18, 2053-2067 (2020).
3. Yuhas, R., Pramuk, K. & Lien, E. L. Human milk fatty acid composition from nine countries varies most in DHA. Lipids 41, 851-858 (2006).
4. Innis, S. M. Dietary Triacylglycerol Structure and Its Role in Infant Nutrition. Adv. Nutr. 2, 275-283 (2011).
5. Leonard, J. M., Slabaugh, M. B. & Knapp, S. J. *Cuphea wrightii* thioesterases have unexpected broad specificities on saturated fatty acids. Plant Mol. Biol. 34, 669-679 (1997).
6. Franklin, S. et al. Tailored oils produced from recombinant heterotrophic microorganisms. (2011).
7. Kim, Y., Terng, E. L., Riekhof, W. R., Cahoon, E. B. & Cerutti, H. Endoplasmic reticulum acyltransferase with prokaryotic substrate preference contributes to triacylglycerol assembly in *Chlamydomonas*. Proc. Natl. Acad. Sci. 201715922 (2018).

TABLE A

In vitro transcription and translation of polycistronic loci. RNAs corresponding to polycistronic transcripts were synthesized from corresponding DNA templates (see methods) and translated in vitro in wheat germ extracts containing [$^{35}$S]-Met. The products were separated by PAGE and visualized by fluorography. The polycistronic gene pairs and their expected sizes are presented as a table. Gene IDs from *C. reinhardtii* begin with "Cre" and gene IDs from *C. zofingiensis* begin with "Cz".

| Lane | Upstream Gene | Size, kDa | Intensity | Downstream Gene | Size, kDa | Intensity |
|---|---|---|---|---|---|---|
| 1 | Cre02.g089000 | 9.5 | 0.5 | Cre02.g088950 | 34.7 | 0.8 |
| 2 | Cre03.g155500 | 6.7 | 0.3 | Cre03.g155501 | 40.8 | 0.5 |
| 3 | Cre06.g278245 | 8.1 | 1.4 | Cre06.g278242 | 14.5 | 0.4 |
| 4 | Cz13g11085 | 7.3 | 1.7 | Cz13g11090 | 13.8 | 0.8 |
| 5 | Cz1na20050 | 8.2 | 1.1 | Cz16g20060 | 32.2 | 0.9 |
| 6 | Cz02g12225 | 10.1 | 1.4 | Cz02g12220 | 37.8 | 0.8 |

TABLE B

Polycistronic expression of exogenous reporter and drug-selectable proteins. Polycistronic loci from *C. reinhardtii* and *C. zofingiensis* in which either the upstream ORF, the downstream ORF, or both were replaced with coding sequences of potential interest for transgenic expression were constructed and subjected to the same analysis described in Table A. mVenus is a YFP analog, and RPS14-Em$^R$ confers resistance to the drug emetine.

| Lane | Upstream Gene | Size, kDa | Intensity | Downstream Gene | Size, kDa | Intensity |
|---|---|---|---|---|---|---|
| 1 | Cz02g12225 | 10.1 | 1.4 | Cz02q12220 | 37.8 | 0.8 |
| 2 | mVenus | 26.9 | 1.9 | Cz02q12220 | 37.8 | 0.2 |
| 3 | Cz02g12225 | 10.1 | 2.7 | mVenus | 26.9 | 0.7 |
| 4 | m Venus | 26.9 | 1.3 | RPS14-Em$^R$ | 16.3 | 0.5 |

TABLE C

Manipulating the upstream Kozak-like sequence alters expression. Three different versions of a polycistronic locus from *C. zofingiensis* were synthesized and subjected to in vitro coupled transcription and translation as in Table A. Each construct contained the same CDSs and inter-cistron sequence for gene 1 (Cz02g35025, 11.0 kDa) and gene 2 (Cz02g35030, 31.8 kDa). Only the nucleotides immediately upstream of the first start codon were altered between the constructs. The construct in lane 1 used the endogenous Kozak-like sequence, while the construct in lane 2 used a strong Kozak-like sequence, and the construct in lane 3 used a weak Kozak-like sequence. The intensities of each band were normalized relative to the number of Met and are presented below the figure.

| Lane | Upstream Gene | Size, kDa | Intensity | Downstream Gene | Size, kDa | Intensity |
|---|---|---|---|---|---|---|
| 1 | Cz02g35025 | 11.0 | 0.4 | Cz02g35030 | 49.0 | 0.4 |
| 2 | Cz02g35025 | 11.0 | 1.0 | Cz02g35030 | 49.0 | 0.3 |
| 3 | Cz02g35025 | 11.0 | 0.3 | Cz02g35030 | 49.0 | 0.6 |

The invention claimed is:

1. A plant transformed with a polycistronic plant locus comprising genes encoding polycistronically co-expressed exogenous proteins, the genes sharing a single promoter, wherein the locus is transcribed in the plant as a corresponding mRNA comprising open reading frames (ORFs) for each of the exogenous proteins and a single poly(A) tail, wherein the ORFs comprise an upstream ORF and a downstream ORF encoding first and second proteins, respectfully, wherein translation of each of the upstream and downstream ORFs is regulated by corresponding upstream and downstream translation initiation sites, that are Kozak-like sequences, tuned to effect a predetermined ratio, that is 3:1 or 0.5:1, of the first and second proteins.

2. The plant of claim 1, wherein the upstream translation initiation site is a strong non-endogenous Kozak-like sequence, increasing the relative expression of the upstream ORF.

3. The plant of claim 1, wherein the upstream translation initiation site is a weak non-endogenous Kozak-like sequence, decreasing the relative expression of the upstream ORF.

4. The plant of claim 1, wherein one of the proteins is a selectable marker.

5. The plant of claim 1, wherein one of the proteins is a selectable marker that is a protein that confers resistance to a drug or herbicide, or complements auxotrophy.

6. The plant of claim 1, wherein the polycistronically-expressed exogenous proteins are enzymes catalyzing corresponding reactions in the plant.

7. A method of recombinant protein production, comprising growing a plant of claim 1, under conditions wherein the plant expresses the proteins.

* * * * *